United States Patent [19]

Houziaux et al.

[11] Patent Number: 5,110,816
[45] Date of Patent: May 5, 1992

[54] 3-[2-(4-ARYLPIPERAZIN-1-YL)ETHOXY]-P-CYMENE, THE DERIVATIVES OF SAID PRODUCT WHICH ARE ORTHO-, META- AND PARA-MONOSUBSTITUTED OR -DISUBSTITUTED ON THE PHENYL RING, THE METHOD OF PREPARING SAID DERIVATIVES AND THE DRUGS IN WHICH SAID COMPOUNDS ARE PRESENT AS THE ACTIVE PRINCIPLE

[75] Inventors: Patrick Houziaux, Maule; Jean-Pierre Riffaud, Versailles; Jean-Yves Lacolle, Saint Nom La Breteche; Bernard Danree, Poissy, all of France

[73] Assignee: Institut de Recherches Chimiques et Biologiques Appliquees (I.R.C.E.B.A.), Vicq, France

[21] Appl. No.: 623,718
[22] PCT Filed: Jun. 13, 1989
[86] PCT No.: PCT/FR89/00298
  § 371 Date: Dec. 12, 1990
  § 102(e) Date: Dec. 12, 1990
[87] PCT Pub. No.: WO89/12634
  PCT Pub. Date: Dec. 28, 1989

[30] Foreign Application Priority Data
  Jun. 13, 1988 [FR] France .................. 88 07864

[51] Int. Cl.$^5$ .................. A61K 31/495; C07D 295/00
[52] U.S. Cl. .................. 514/255; 544/392; 544/394
[58] Field of Search .................. 514/255; 544/392, 394

[56] References Cited
U.S. PATENT DOCUMENTS
  4,698,343 10/1987 Creuzet et al. .................. 544/394
  4,721,715 1/1988 Creuzet et al. .................. 544/394

FOREIGN PATENT DOCUMENTS
  743494  6/1970 Belgium .................. 544/394
  78756   5/1983 European Pat. Off. .................. 544/394
  78757   5/1983 European Pat. Off. .................. 544/394
  0173634 3/1986 European Pat. Off. .
  0237411 9/1987 European Pat. Off. .
  3604941 8/1987 Fed. Rep. of Germany .................. 544/394
  1349636 2/1963 France .................. 544/394
  3734    4/1964 France .................. 544/394

Primary Examiner—Cecilia Shen
Attorney, Agent, or Firm—Webb, Burden, Ziesenheim & Webb

[57] ABSTRACT

The present invention relates to the products of general formula (I):

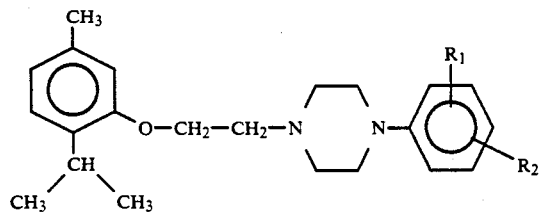

in which $R_1$ and $R_2$ are identical or different and are selected from a hydrogen atom, a halogen atom, a hydroxyl radical, an alkyl radical having from 1 to 5 (sic) carbon atoms, an alkoxy radical having from 1 to 5 carbon atoms or a phenoxy, benzyloxy, trifluoromethyl or acetyl radical.

It further relates to
a method of preparing said products
and the drugs in which said products are present.

3 Claims, No Drawings

3-[2-(4-ARYLPIPERAZIN-1-YL)ETHOXY]-P-CYMENE, THE DERIVATIVES OF SAID PRODUCT WHICH ARE ORTHO-, META- AND PARA-MONOSUBSTITUTED OR -DISUBSTITUTED ON THE PHENYL RING, THE METHOD OF PREPARING SAID DERIVATIVES AND THE DRUGS IN WHICH SAID COMPOUNDS ARE PRESENT AS THE ACTIVE PRINCIPLE

The present invention relates, by way of novel products, to 3-[2-(4-phenylpiperazin-1-yl)ethoxy]-p-cymene and its derivatives which are ortho-, meta- and para-monosubstituted or —disubstituted on the phenyl ring and to a method of preparing these derivatives; it further relates to the drugs in which at least one of said compounds is present as the active principle.

The chemical products according to the invention have the general formula

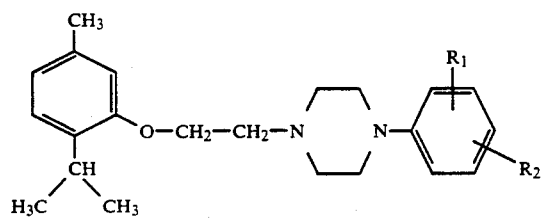

$R_1$ and $R_2$, which are identical or different, being selected from a hydrogen atom, a halogen atom, a hydroxyl radical, an alkyl radical having from 1 to 4 carbon atoms, an alkoxy radical having from 1 to 5 carbon atoms or a phenoxy, benzyloxy, trifluoromethyl or acetyl radical.

In formula I, the alkyl or alkoxy groups can have a linear or branched chain.

An alkyl group having from 1 to 5 carbon atoms is for example a methyl, ethyl, propyl, isopropyl, butyl, sec-butyl or tert-butyl group, preferably a methyl group.

An alkoxy group having from 1 to 5 carbon atoms is for example a methoxy, ethoxy, propoxy, isopropoxy, butoxy, isobutoxy, neopentoxy, pentoxy or isopentoxy group, preferably an ethoxy or isopropoxy group.

A halogen atom is preferably a chlorine atom.

The products according to the invention can also take the form of the salts of the products of formula (I) with a pharmaceutically acceptable mineral acid such as, for example, hydrochloric acid or sulfuric acid, or a pharmaceutically acceptable organic acid such as, for example, citric, tartaric, malic, maleic, fumaric or methanesulfonic acid.

The derivatives of p-cymene which are disubstituted in the 3-position and in the 6-position are already known and have cardiovascular and antiallergic activities. References which may be mentioned are the patents FR-2 570 376 and EP-179009, in which the substituent in the 3-position is an alkoxy substituted by a phenylpiperazine and in which the substituent in the 6-position is an aminohydroxyalkoxy, whereas in the patent EP-173634, the substituent in the 6-position is a hydroxyl.

In the present invention, the p-cymene is substituted only in the 3-position by an alkoxy. It is therefore a thymol derivative and consequently the compound is novel.

The products of the invention are manufactured from 3-(2-chloroethoxy)-p-cymene of formula (II) and the 1-(substituted phenyl)piperazine of formula (III) according to the following general reaction scheme:

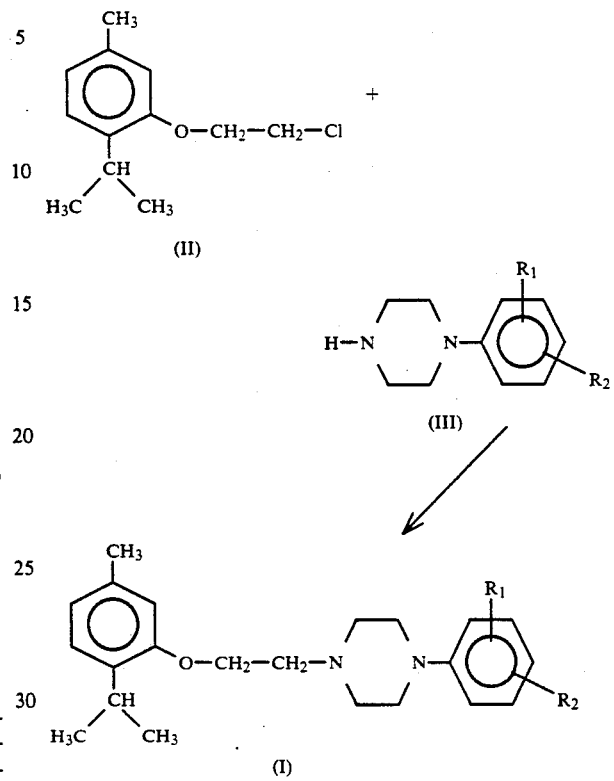

$R_1$ and $R_2$ being defined above.

The number of mol of compound (III) is approximately twice the number of mol of compound (II).

The pharmaceutically acceptable salts, for example the hydrochlorides, are obtained in known manner by bringing a solution of the product of formula (I) into contact with the acid in question (for example by bubbling hydrochloric acid into a solution of the product of formula (I)). Furthermore, these salts can contain one or two mol of salifying acid per mol of product of formula (I).

The present invention further relates to the drugs containing at least one product of formula (I) as the active product; said drugs can be useful especially in the field of urology.

The non-limiting Examples which follow illustrate the methods of preparing the products according to the invention.

The AgNO$_3$ test is a test for product purity.

EXAMPLE 1

Synthesis of 3-[2-(4-p-fluorophenylpiperazin-1-yl)ethoxy]-p-cymene dihydrochloride. Codename=B 1055. Product of formula (I) where $R_1$=4-fluoro, in the form of the dihydrochloride.

1. Preparation of 3-[2-(4-p-fluorophenylpiperazin-1-yl)ethoxyl]-p-cymene

The following are introduced into a 100 ml three-necked flask fitted with a condenser, a magnetic stirrer and a thermometer:

21.27 g (0.1 mol) of 3-(2-chloroethoxy)-p-cymene 43.2 g (0.24 mol) of 1-p-fluorophenylpiperazine.

The mixture is heated at 140° C. for 10 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vaccum to give 48.8 g of crude product.

This was topped by fractional distillation under vacuum (under nitrogen).

35.3 g of residue are isolated and recrystallized from 40 ml of hexane to give 29.95 g of beige crystals (yield=84%); m.p.$_{KB}$=53°-54° C.; GC purity >99%.

2. Preparation of the dihydrochloride 17.82 g (0.05 mol) of this product are dissolved in anhydrous ethyl ether. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 19.53 g of beige crystals (crude yield=91%).

After recrystallization from isopropanol, 16.10 g of a white product are isolated (yield after recrystallization=74.9%).

Said crystals have an m.p.$_{KB}$ of 157°-162° C., IR and NMR spectra consistent with the proposed structure and an AgNO$_3$ titer of 100%.

EXAMPLE 2

Synthesis of 3-[2-(4-phenylpiperazin-1-yl)ethoxy]-p-cymene dihydrochloride. Codename=B 1057. Product of formula (I) where R$_1$=R$_2$=H, in the form of the dihydrochloride.

1. Preparation of 3-[2-(4-phenylpiperazin-1-yl)ethoxy]-p-cymene.

The following are introduced into a 100 ml three-necked flask fitted with a condenser, a magnetic stirrer and a thermometer:

21.27 g (0.1 mol) of 3-(2-chloroethoxy)-p-cymene 38.93 g (0.24 mol) of N-phenylpiperazine.

The mixture is heated at 140° C. for 10 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 44.7 g of crude product.

This is purified by fractional distillation under vacuum (under nitrogen). 32.15 g of a residue are isolated and recrystallized from a 3/1 pentane/hexane mixture to give 29.85 g of beige crystals (yield=82.2%); m.p.$_{KB}$=71°-72° C.; GC purity >99%.

2. Preparation of the dihydrochloride 16.92 g (0.05 mol) of this product are dissolved in anhydrous ethyl ether. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 19.5 g of beige crystals (crude yield=94.8%).

After recrystallization from isopropanol, 14.8 g of a white product are isolated (yield after recrystallization=72%).

Said crystals have an m.p.$_{KB}$ of 162°-164° C., IR and NMR spectra consistent with the proposed structure and an AgNO$_3$ titer of 97.5%. Elemental analysis (empirical formula: $C_{22}H_{32}Cl_2N_2O$) gave the following results:

| % | Calculated | Found |
|---|---|---|
| C | 63.88 | 64.30 |
| H | 7.86 | 7.84 |
| Cl | 17.14 | 17.36 |
| N | 6.77 | 6.74 |
| O | 4.35 | 4.24 |

EXAMPLE 3

Synthesis of 3-[2-(4-α,α,α-trifluoro-m-tolylpiperazin-1-yl)ethoxy]-p-cymene monohydrochloride. Codename=B 1079.

Product of formula (I) where R$_1$=3-trifluoromethyl, in the form of the hydrochloride

1. Preparation of 3-[2-(4-α,α,α-trifluoro-m-tolylpiperazin-1-yl)ethoxy]-p-cymene The following are introduced into a 100 ml three-necked flask fitted with a condenser, a magnetic stirrer and a thermometer:

21.27 g (0.1 mol) of 3-(2-chloroethoxy)-p-cymene 46.05 g (0.2 mol) of N-(α,α,α-trifluoro-m-tolyl)piperazine.

The mixture is heated at 140° C. for 5 hours.

After cooling to room temperature, the reaction medium is poured into a 10% solution of sodium bicarbonate. The aqueous phase obtained is extracted with twice 100 ml of methylene chloride. The combined organic phases are washed with a saturated aqueous solution of sodium chloride. They are then dried over sodium sulfate. After filtration, the solvent is driven off under vacuum to give 56.46 g of crude product.

This is purified by fractional distillation under vacuum (under nitrogen).

23.62 g of a yellow oil are isolated (yield=58.1%).

The product obtained has a boiling point (under 0.15 mm Hg) of 195° C. and IR and NMR spectra consistent with the proposed structure.

2. Preparation of the hydrochloride 20.32 g (0.05 mol) of this product are dissolved in anhydrous methylene chloride. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 14.48 g of beige crystals (crude yield=65.4%).

After recrystallization from ethanol, 5.91 g of a white product are isolated (yield after recrystallization=26.7%).

Said crystals have an m.p.$_{KB}$ of 146°-148° C., IR and NMR spectra consistent with the proposed structure and an AgNO$_3$ titer of 101%.

EXAMPLE 4

Synthesis of 3-[2-(4-p-acetylphenylpiperazin-1-yl)ethoxy]-p-cymene hydrochloride. Codename=B 1105. Product of formula (I) where R$_1$=4-acetyl, in the form of the hydrochloride 1. Preparation of 3-[2-(4-p-acetylphenylpiperazin-1-yl)ethoxy]-p-cymene.

The following are introduced into a 100 ml three-necked flask fitted with a condenser, a magnetic stirrer and a thermometer:
21.27 g (0.1 mol) of 3-(2-chloroethoxy)-p-cymene
40.85 g (0.2 mol) of p-piperazinylacetophenone
The mixture is heated at 145° C. for 1 hour.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 59.3 g of crude product.

This is topped by fractional distillation under vacuum (under nitrogen).

27.66 g of a residue are isolated and recrystallized from a 5/2 IPA/ethanol mixture.

This gives 11.22 g of beige crystals (yield=29.5%); m.p.$_{KB}$=90°-92° C.; GC purity >99%; perchloric titer=102%; IR: consistent with the proposed structure.

2. Preparation of the hydrochloride 9.51 g (0.025 mol) of this product are dissolved in an anhydrous ethyl ether/methylene chloride mixture (15/1). The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 10 g of beige crystals (crude yield=96%).

After recrystallization from toluene, 7.45 g of a white product are isolated (yield after recrystallization=71.5%).

Said crystals have an m.p.$_{KB}$ of 150°-152° C., IR and NMR spectra consistent with the proposed structure and an AgNO$_3$ titer of 103.6%.

EXAMPLE 5

Synthesis of 3-[2-(4-p-methoxyphenylpiperazin-1-yl)ethoxy]-p-cymene dihydrochloride. Codename=B 1115. Product of formula (I) where R$_1$=4-methoxy, in the form of the dihydrochloride 1. Preparation of 3-[2-(4-p-methoxyphenylpiperazin-1-yl)ethoxy]-p-cymene The following are introduced into a 100 ml three-necked flask fitted with a condenser, a magnetic stirrer and a thermometer:
21.27 g (0.1 mol) of 3-(2-chloroethoxy)-p-cymene
38.45 g (0.2 mol) of 1-p-methoxyphenylpiperazine.
The mixture is heated at 140° C. for 10 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 56.27 g of crude product.

This is purified by fractional distillation under vacuum (under nitrogen).

17.43 g of a yellowish liquid are isolated (yield=47.3%); b.p.$_{0.3\ mm\ Hg}$=206°-210° C.

2. Preparation of the dihydrochloride 9.2 g (0.025 mol) of this product are dissolved in 100 ml of anhydrous methylene chloride. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 10.02 g of brown crystals (crude yield=90.8%).

After recrystallization from a ½ ethyl ether/ IPA mixture, 5.36 g of a white product are isolated (yield after recrystallization=48.6%).

Said crystals have an m.p.$_{KB}$ of 162°-164° C.,IR and NMR spectra consistent with the proposed structure and an AgNO$_3$ titer of 98.6%.

EXAMPLE 6

Synthesis of 3-[2-4-(4-chloro-2-methyl)phenylpiperazine-1-yl)ethoxy]-p-cymene hydrochloride. Codename=B 1152. Product of formula (I) where R$_1$=2-methyl; R$_2$=4-chloro, in the form of the hydrochloride.

1. Preparation of 3-[2-4-(4-chloro-2-methyl)phenylpiperazin-1-yl)ethoxy]-p-cymene The following are introduced into a 100 ml three-necked flask fitted with a condenser, a magnetic stirrer and a thermometer:
21.27 g (0.1 mol) of 3-(2-chloroethoxy)-p-cymene
42.14 g (0.2 mol) of 1-(4-chloro-2-methyl)phenylpiperazine.
The mixture is heated at 140° C. for 5 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 44.60 g of crude product.

This is purified by fractional distillation under vacuum (under nitrogen).

33.48 g of distilled product are isolated (yield=86.5%); b.p.$_{0.1\ mm\ Hg}$=215°-217° C.; perchloric titer=100.3%.

2. Preparation of the hydrochloride 19.35 g (0.05 mol) of this product are dissolved in anhydrous ethyl ether. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 23.31 g of beige crystals.

After recrystallization from a 6/1 ethyl acetate/ethanol mixture, 7.11 g of a white product are isolated (yield after recrystallization = 31.9%).

Said crystals have an m.p.$_{KB}$ of 178°–180° C., IR and NMR spectra consistent with the proposed structure and an AgNO$_3$ titer of 100.4%.

EXAMPLE 7

Synthesis of 3-[2-(4-o-methoxyphenylpiperazin-1-yl)-ethoxy]-p-cymene dihydrochloride. Codename = B 1168. Product of formula (I) where R$_1$ = 2-methoxy, in the form of the dihydrochloride

1. Preparation of 3-[2-(4-o-methoxyphenylpiperazin-1-yl)ethoxy]-p-cymene.

The following are introduced into a 100 ml three-necked flask fitted with a condenser, a magnetic stirrer and a thermometer:

21.27 g (0.1 mol) of 3-(2-chloroethoxy)-p-cymene
38.45 g (0.2 mol) of 1-o-methoxyphenylpiperazine.

The mixture is heated at 100° C. for 10 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 35.49 g of crude product (yield = 96.3%).

2. Preparation of the dihydrochloride 18.43 g (0.05 mol) of this crude product are dissolved in anhydrous ethyl ether. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 21.23 g of beige crystals (crude yield = 96.2%).

After recrystallization from a 3/2 ethyl acetate/isopropanol mixture, 15.54 g of a white product are isolated (yield after recrystallization = 70.4%).

Said crystals have an m.p.$_{KB}$ of 150°–160° C., IR and NMR spectra consistent with the proposed structure and an AgNO$_3$ titer of 98.2%.

EXAMPLE 8

Synthesis of 3-[2-(4-o-ethoxyphenylpiperazin-1-yl)ethoxy]-p-cymene dihydrochloride. Codename = B 1178. Product of formula (I) where R$_1$ = 2-ethoxy, in the form of the dihydrochloride

1. Preparation of 3-[2-(4-o-ethoxyphenylpiperazin-1-yl)ethoxyl]-p-cymene.

The following are introduced into a 100 ml three-necked flask fitted with a condenser, a magnetic stirrer and a thermometer:

21.27 g (0.1 mol) of 3-(2-chloroethoxy)-p-cymene
43.32 g (0.21 mol) of 1-(2-ethoxyphenyl)piperazine.

The mixture is heated at 100° C. for 18 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 40.40 g of crude product.

2. Preparation of the dihydrochloride 22.77 g (0.05 mol) of this crude product are dissolved in anhydrous ethyl ether. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 19.86 g of beige crystals (crude yield = 87.2%).

After recrystallization from a ⅜ ethyl acetate/isopropanol mixture, 5.87 g of a white product are isolated (yield after recrystallization = 25.8%).

Said crystals have an m.p.$_{KB}$ of 145°–150° C., IR and NMR spectra consistent with the proposed structure and an AgNO$_3$ titer of 97.6%.

Elemental analysis (empirical formula: $C_{24}H_{36}Cl_2N_2O_2$) gave the following results:

| % | Calculated | Found |
| --- | --- | --- |
| C | 63.14 | 63.14 |
| H | 7.98 | 7.87 |
| Cl | 15.53 | 15.81 |
| N | 6.13 | 6.15 |
| O | 7.22 | 7.34 |

EXAMPLE 9

Synthesis of 3-[2-4-(3,4-dichloro)phenylpiperazin-1-yl)ethoxy]-p-cymene hydrochloride. Codename = B 1184. Product of formula (I) where R$_1$ = 3-chloro; R$_2$ = 4-chloro, in the form of the hydrochloride.

1. Preparation of 3-[2-4-(3,4-dichloro)phenylpiperazin-1-yl)ethoxyl]-p-cymene The following are introduced into a 100 ml three-necked flask fitted with a condenser, a magnetic stirrer and a thermometer:

21.27 g (0.1 mol) of 3-(2-chloroethoxy)-p-cymene
48.53 g (0.21 mol) of 1-(3,4-dichloro)phenylpiperazine.

The mixture is heated at 100° C. for 26 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 40.61 g of crude product.

This is purified by column chromatography under pressure on a silica gel support (60–200μ).

30.47 g of a crystalline product are isolated (yield 74.8%).

2. Preparation of the hydrochloride 20.37 g (0.05 mol) of this product are dissolved in anhydrous ethyl ether. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 16.11 g of beige crystals (crude yield=72.6%).

After recrystallization from an 8/1 ethyl acetate/isopropanol mixture, 13.89 g of a white product are isolated (yield after recrystallization=62.6%).

Said crystals have an m.p.$_{KB}$ of 170°–172° C., IR and NMR spectra consistent with the proposed structure and an AgNO$_3$ titer of 95.2%.

EXAMPLE 10

Synthesis of 3-[2-(4-p-chlorophenylpiperazin-1-yl)ethoxy]-p-cymene dihydrochloride. Codename=B 1191. Product of the formula (I) where R$_1$=4-chloro, in the form of the dihydrochloride.

1. Preparation of 3-[2-(4-p-chlorophenylpiperazin-1-yl)ethoxy]-p-cymene.

The following are introduced into a 100 ml three-necked flask fitted with a condenser, a magnetic stirrer and a thermometer:

21.27 g (0.1 mol) of 3-(2-chloroethoxy)-p-cymene
41.30 g (0.21 mol) of 1-p-chlorophenylpiperazine The mixture is heated at 100° C. for 28 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 34.01 g of crude product (yield=91.2%).

2. Preparation of the dihydrochloride 18.65 g (0.05 mol) of this product are dissolved in anhydrous ethyl ether. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 22.29 g of beige crystals (crude yield=100%).

After recrystallization from ethanol, 14.80 g of a white product are isolated (yield after recrystallization=66.4%).

Said crystals have an m.p.$_{KB}$ of 165°–167° C., IR and NMR spectra consistent with the proposed structure and an AgNO$_3$ titer of 97.5%.

EXAMPLE 11

Synthesis of 3-[2-(4-m-ethoxyphenylpiperazin-1-yl)ethoxy]-p-cymene hydrochlroide. Codename B 1204. Product of formula (I) were R$_1$=3-ethoxy, in the form of the hydrochloride.

1. Preparation of 3-[2-(4-m-ethoxyphenylpiperazin-1-yl)ethoxy]-p-cymene

The following are introduced into a 100 ml three-necked flask fitted with a condenser, a magnetic stirrer and a thermometer:

21.27 g (0.1 mol) of 3-(2-chloroethoxy)-p-cymene
43.32 g (0.21 mol) of 1-m-ethoxyphenylpiperazine The mixture is heated at 100° C. for 33 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 38.40 g of crude product.

This product is purified by column chromatography under pressure on a silica gel support (60–200μ). 32.17 g of a brown liquid product are isolated (yield=84.1%).

2. Preparation of the hydrochloride 19.13 g (0.05 mol) of this product are dissolved in anhydrous ethyl ether. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 19.59 g of beige crystals (crude yield: 93.5%).

After recrystallization from acetone, 11.88 g of a white product are isolated (yield after recrystallization=56.7%).

Said crystals have an m.p.$_{KB}$ of 169°–170° C., IR and NMR spectra consistent with the proposed structure and an AgNO$_3$ titer of 109.1%.

EXAMPLE 12

Synthesis of 3-[2-(4-m-methoxyphenylpiperazin-1-yl)ethoxy]-p-cymene hydrochloride. Codename=B 1206. Product of formula (I) where R$_1$=3-methoxy, in the form of the hydrochloride.

1. Preparation of 3-[2-(4-m-methoxyphenylpiperazin-1-yl)ethoxy]-p-cymene.

The following are introduced into a 100 ml three-necked flask fitted with a condenser, a magnetic stirrer and a thermometer:

21.27 g (0.1 mol) of 3-(2-chloroethoxy)-p-cymene
40.37 g (0.21 mol) of 1-m-methoxyphenylpiperazine The mixture is heated at 100° C. for 25 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 41.20 g of crude product.

This product is purified by column chromatography under pressure on a silica gel support (60–200 μ). 28.26 g of a brown liquid are isolated (yield=76.7%).

2. Preparation of the hydrochloride 18.47 g (0.05 mol) of this product are dissolved in ethanol. An ethanolic solution of HCl (containing 0.05 mol of gaseous HCl) is added. After partial concentration under vacuum and precipitation with anhydrous ethyl ether, the crystals formed are filtered off on a glass frit, washed with anhydrous ethyl ether and then dried under vacuum over potassium hydroxide at 70° C.

This gives 19.48 g of beige crystals (crude yield=96.2%).

After recrystallization from a 4/1 isopropanol/ethanol mixture, 16.56 g of a white product are isolated (yield after recrystallization=81.8%).

Said crystals have an m.p.$_{KB}$ of 190°-192° C., IR and NMR spectra consistent with the proposed structure and an AgNO$_3$ titer of 99.6%.

EXAMPLE 13

Synthesis of 3-[2-(4-o-methylphenylpiperazin-1-yl)-ethoxy]-p-cymene hydrochloride. Codename=B 1213. Product of formula (I) where R$_1$=2-methyl, in the form of the hydrochloride.

1. Preparation of 3-[2-(4-o-methylphenylpiperazin-1-yl)ethoxy]-p-cymene.

The following are introduced into a 100 ml three-necked flask fitted with a condenser, a magnetic stirrer and a thermometer:

21.27 g (0.1 mol) of 3-(2-chloroethoxy)-p-cymene
37.02 g (0.21 mol) of 1-o-tolylpiperazine.

The mixture is heated at 100° C. for 18 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 49 g of crude product.

This product is purified by column chromatography under pressure on a silica gel support (60-200 μ). 25.52 g of a brown liquid are isolated (yield=72.4%).

2. Preparation of the hydrochloride 17.62 g (0.05 mol) of this product are dissolved in ethanol. An ethanolic solution of HCl (containing 0.05 mol of gaseous HCl) is added. After partial concentration under vacuum and precipitation with anhydrous pentane, the crystals formed are filtered off on a glass frit, washed with anhydrous ethyl ether and then dried under vacuum over potassium hydroxide at 70° C.

This gives 18.67 g of crystals (crude yield×96%).

After recrystallization from ethyl acetate, 16.90 g of a white product are isolated (yield after recrystallization=86.9%).

Said crystals have an m.p.$_{KB}$ of 158°-160° C., IR and NMR spectra consistent with the proposed structure and an AgNO$_3$ titer of 100.9%.

EXAMPLE 14

Synthesis of 3-[2-4-(2-methyl-5-chlorophenyl)piperazin-1-yl)ethoxy]-p-cymene hydrochloride. Codename=B 1256. Product of formula (I) where R$_1$=2-methyl; R$_2$=5-chloro, in the form of the hydrochloride 1. Preparation of 3-[2-4-(2-methyl-5-chlorophenyl)piperazin-1-yl)ethoxy]-p-cymene The following are introduced into a 100 ml three-necked flask fitted with a condenser, a magnetic stirrer and a thermometer:

21.27 g (0.1 mol) of 3-(2-chloroethoxy)-p-cymene
44.25 g (0.21 mol) of 1-(2-methyl-5-chloro)phenylpiperazine The mixture is heated at 100° C. for 60 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 40.70 g of crude product.

This product is purified by fractional distillation under vacuum (under nitrogen).

26 g of a yellow liquid are isolated (yield= 67.2%); b.p.$_{0.15 \, mm \, Hg}$=225°-230° C.

2. Preparation of the hydrochloride 19.35 g (0.05 mol) of this product are dissolved in anhydrous ethyl ether. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 21.17 g of beige crystals (crude yield=100%).

After recrystallization from ethyl acetate, 8.28 g of a white product are isolated (yield after recrystallization=39.1%).

Said crystals have an m.p.$_{KB}$ of 166°-168° C., IR and NMR spectra consistent with the proposed structure and an AgNO$_3$ titer of 100.4%.

EXAMPLE 15

Synthesis of 3-[2-(4-o-fluorophenylpiperazin-1-yl)ethoxy]-p-cymene hydrochloride. Codename=B 1261. Product of formula (I) where R$_1$=2-fluoro, in the form of the hydrochloride 1. Preparation of 3-[2-(4-o-fluorophenylpiperazin-1-yl)ethoxy]-p-cymene The following are introduced into a 100 ml three-necked flask fitted with a condenser, a magnetic stirrer and a thermometer:

21.27 g (0.1 mol) of 3-(2-chloroethoxy)-p-cymene
37.85 g (0.21 mol) of 1-o-fluorophenylpiperazine The mixture is heated at 100° C. for 33 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 38.85 g of crude product.

This product is topped by fractional distillation under vacuum (under nitrogen). The residue is taken up in ethyl ether and filtered off on paper. The filtrate is concentrated to dryness under vacuum.

28.66 g of a brown oil are isolated (yield=80.4%).

2. Preparation of the hydrochloride 17.83 g (0.05 mol) of this product are dissolved in anhydrous ethyl ether. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 17.96 g of grayish crystals (yield=91.4%).

After recrystallization from a 50/50 pentane/isopropanol mixture, 13.16 g of a white product are isolated (yield after recrystallization=67%).

Said crystals have an m.p.$_{KB}$ of 180°–185° C., IR and NMR spectra consistent with the proposed structure and an AgNO$_3$ titer of 99.4%.

EXAMPLE 16

Synthesis of 3-[2-(4-o-chlorophenylpiperazin-1-yl)ethoxy]-p-cymene hydrochloride. Codename=B 1299. Product of formula (I) where R$_1$=2-chloro, in the form of the hydrochloride.

1. Preparation of 3-[2-(4-o-chlorophenylpiperazin-1-yl)ethoxy]-p-cymene

The following are introduced into a 100 ml three-necked flask fitted with a condenser, a magnetic stirrer and a thermometer:

21.27 g (0.1 mol) of 3-(2-chloroethoxy)-p-cymene
41.30 g (0.21 mol) of 1-o-chlorophenylpiperazine The mixture is heated at 100° C. for 25 hours.

After cooling to room temperature, the reaction medium is poured into a 10% solution of sodium bicarbonate. The aqueous phase obtained is extracted twice with 100 ml of methylene chloride. The combined organic phases are washed with a saturated aqueous solution of sodium chloride. They are then dried over sodium sulfate. After filtration, the solvent is driven off under vacuum to give 38.14 g of crude product.

This product is purified by fractional distillation under vacuum (under nitrogen).

23.90 g of a yellow oil are isolated, b.p.o.1 mm Hg=195°–197° C. (yield=64.1%).

2. Preparation of the hydrochloride 18.64 g (0.05 mol) of this product are dissolved in anhydrous ethyl ether. The solution is saturated with a stream of dry hydrogen chloride on an ice bath. The crystals formed are filtered off on a glass frit, washed with anhydrous ethyl ether and then dried under vacuum over potassium hydroxide at 70° C.

This gives 19.55 g of beige crystals (yield=95.5%).

After recrystallization from ethyl acetate, 14.29 g of a white product are isolated (yield after recrystallization=69.8%).

Said crystals have an m.p.KB of 136°–138° C., IR and NMR spectra consistent with the proposed structure and an AgNO$_3$ titer of 98.5%.

EXAMPLES 17 to 32

Other compounds were prepared using experimental procedures analogous to those described in Examples 1 to 16, which those skilled in the art will readily work out; Table I gives the empirical formula, the molecular weight, the melting point and the AgNO$_3$ titer of said compounds.

The Table below is a summary of the products exemplified in this patent.

SUMMARY TABLE OF THE PRODUCTS EXEMPLIFIED
GENERAL FORMULA:

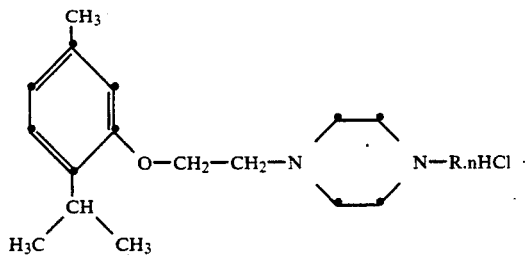

| Example | R | n | Code B | Empirical formula | MW | M.p.KB (°C.) | AgNO$_3$ titer of the hydrochloride |
|---|---|---|---|---|---|---|---|
| 1 | ⟨⟩—F | 2 | 1055 | C$_{22}$H$_{31}$Cl$_2$FN$_2$O | 429.45 | 157–162 | 100% |
| 2 | ⟨⟩ | 2 | 1057 | C$_{22}$H$_{32}$Cl$_2$N$_2$O | 411.41 | 162–164 | 97.5% |
| 3 | ⟨⟩—CF$_3$ | 1 | 1079 | C$_{23}$H$_{30}$ClF$_3$N$_2$O | 442.95 | 146–148 | 101% |
| 4 | ⟨⟩—C(=O)—CH$_3$ | 1 | 1105 | C$_{24}$H$_{33}$ClN$_2$O$_2$ | 416.98 | 150–152 | 103.6% |

-continued

SUMMARY TABLE OF THE PRODUCTS EXEMPLIFIED
GENERAL FORMULA:

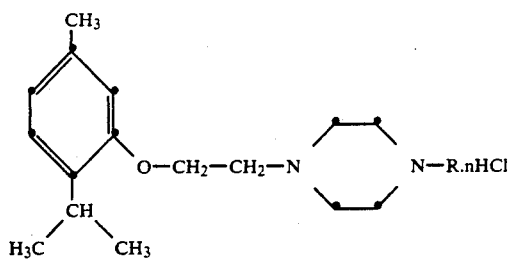

| Example | R | n | Code B | Empirical formula | MW | M.p.KB (°C.) | AgNO$_3$ titer of the hydrochloride |
|---|---|---|---|---|---|---|---|
| 5 | ⌬—O—CH$_3$ | 2 | 1115 | C$_{23}$H$_{34}$Cl$_2$N$_2$O$_2$ | 441.43 | 162–164 | 98.6% |
| 6 | ⌬—Cl, CH$_3$ | 1 | 1152 | C$_{23}$H$_{32}$Cl$_2$N$_2$O | 423.42 | 178–180 | 100.4% |
| 7 | ⌬—O—CH$_3$ | 2 | 1168 | C$_{23}$H$_{34}$Cl$_2$N$_2$O$_2$ | 441.43 | 150–160 | 98.2% |
| 8 | ⌬—O—C$_2$H$_5$ | 2 | 1178 | C$_{24}$H$_{36}$Cl$_2$N$_2$O$_2$ | 455.47 | 145–150 | 97.6% |
| 9 | ⌬—Cl, Cl | 1 | 1184 | C$_{22}$H$_{29}$Cl$_3$N$_2$O | 443.83 | 170–172 | 95.2% |
| 10 | ⌬—Cl | 2 | 1191 | C$_{22}$H$_{31}$Cl$_3$N$_2$O | 445.85 | 165–167 | 97.5% |
| 11 | ⌬—O—C$_2$H$_5$ | 1 | 1204 | C$_{24}$H$_{35}$ClN$_2$O$_2$ | 419.0 | 169–170 | 109.1% |
| 12 | ⌬—O—CH$_3$ | 1 | 1206 | C$_{23}$H$_{33}$ClN$_2$O$_2$ | 404.97 | 190–192 | 99.6% |

-continued

SUMMARY TABLE OF THE PRODUCTS EXEMPLIFIED

GENERAL FORMULA:

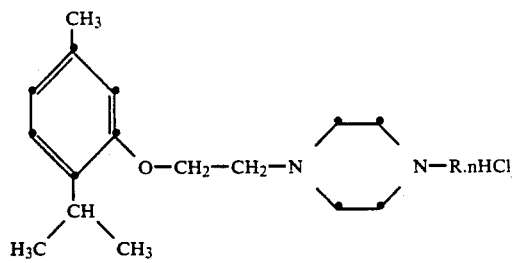

| Example | R | n | Code B | Empirical formula | MW | M.p.KB (°C.) | AgNO$_3$ titer of the hydrochloride |
|---|---|---|---|---|---|---|---|
| 13 | 4-methylphenyl (CH$_3$) | 1 | 1213 | C$_{23}$H$_{33}$ClN$_2$O | 388.98 | 158–160 | 100.9% |
| 14 | 2-methyl-4-chlorophenyl (CH$_3$, Cl) | 1 | 1256 | C$_{23}$H$_{32}$Cl$_2$N$_2$O | 423.43 | 166–168 | 100.4% |
| 15 | 4-fluorophenyl (F) | 1 | 1261 | C$_{22}$H$_{30}$ClFN$_2$O | 392.94 | 180–185 | 99.4% |
| 16 | 4-chlorophenyl (Cl) | 1 | 1299 | C$_{22}$H$_{30}$Cl$_2$N$_2$O | 409.40 | 136–138 | 98.5% |
| 17 | 2-methyl-4-chlorophenyl (CH$_3$, Cl) | 1 | 1326 | C$_{23}$H$_{32}$Cl$_2$N$_2$O | 423.43 | 168–170 | 97.9% |
| 18 | 4-hydroxyphenyl (OH) | 1 | 1338 | C$_{22}$H$_{31}$ClN$_2$O$_2$ 0.5 H$_2$O | 399.95 | 170–172 | 101.6% |
| 19 | 2-methyl-4-butoxyphenyl (CH$_3$—(CH$_2$)$_3$—O) | 1 | 1340 | C$_{26}$H$_{39}$ClN$_2$O$_2$ | 447.07 | 154–156 | 98.6% |

SUMMARY TABLE OF THE PRODUCTS EXEMPLIFIED
GENERAL FORMULA:

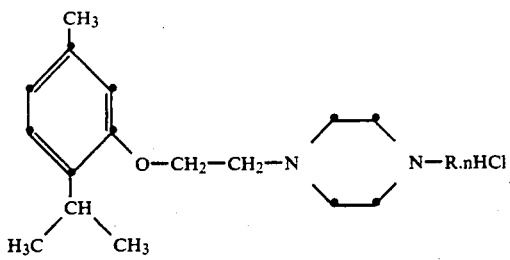

| Example | R | n | Code B | Empirical formula | MW | M.p.KB (°C.) | AgNO$_3$ titer of the hydrochloride |
|---|---|---|---|---|---|---|---|
| 20 | (phenyl-OH) | 1 | 1343 | C$_{22}$H$_{31}$ClN$_2$O$_2$ | 390.95 | 183–184 | 98.6% |
| 21 | (Cl, CH$_3$-phenyl) | 1 | 1353 | C$_{23}$H$_{32}$Cl$_2$N$_2$O | 423.41 | 172–173 | 99% |
| 22 | (CH$_3$—(CH$_2$)$_4$—O-phenyl) | 1 | 1356 | C$_{27}$H$_{41}$ClN$_2$O$_2$ | 462.0 | 146–148 | 98.3% |
| 23 | (CH$_3$—(CH$_2$)$_2$—O-phenyl) | 1 | 1358 | C$_{25}$H$_{37}$ClN$_2$O$_2$ | 433.04 | 169–171 | 99.3% |
| 24 | (O—CH$_3$, CH$_3$—O-phenyl) | 1 | 1362 | C$_{24}$H$_{35}$ClN$_2$O$_3$ | 435.00 | 170–172 | 99% |
| 25 | (O—CH$_3$, CH$_3$—O-phenyl) | 1 | 1387 | C$_{24}$H$_{35}$ClN$_2$O$_3$ | 435.00 | 176–178 | 99.4% |
| 26 | (CH$_3$, CH$_3$-phenyl) | 1 | 1393 | C$_{24}$H$_{35}$ClN$_2$O | 403.00 | 174–175 | 100.1% |

-continued
SUMMARY TABLE OF THE PRODUCTS EXEMPLIFIED
GENERAL FORMULA:
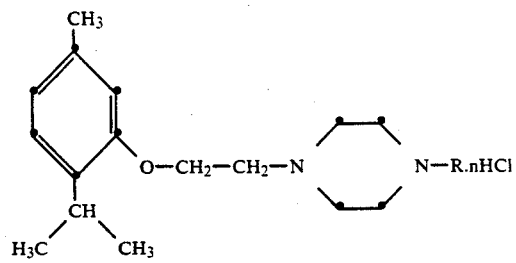
| Example | R | n | Code B | Empirical formula | MW | M.p.KB (°C.) | AgNO$_3$ titer of the hydrochloride |
|---|---|---|---|---|---|---|---|
| 27 | 4-isopropylphenoxy | 1 | 1399 | C$_{25}$H$_{37}$ClN$_2$O$_2$ | 433.04 | 208–210 | 95.6% |
| 28 | 4-phenylphenoxy | 1 | 1410 | C$_{28}$H$_{35}$ClN$_2$O$_2$ | 467.05 | 168–170 | 97% |
| 29 | 4-benzylphenoxy | 1 | 1411 | C$_{29}$H$_{37}$ClN$_2$O$_2$ | 481.08 | 181–182 | 97.4% |
| 30 | 4-neopentylphenoxy | 1 | 1412 | C$_{27}$H$_{41}$ClN$_2$O$_2$ | 461.09 | 220–222 | 98.5% |
| 31 | 4-isobutylphenoxy | 1 | 1413 | C$_{26}$H$_{39}$ClN$_2$O$_2$ | 447.06 | 192–194 | 99.2% |

SUMMARY TABLE OF THE PRODUCTS EXEMPLIFIED
GENERAL FORMULA:

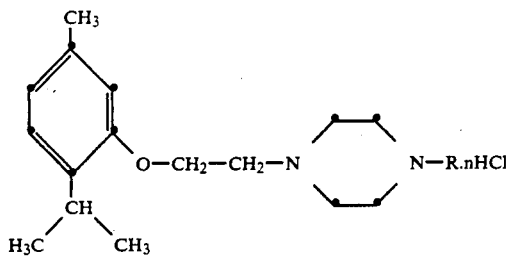

| Example | R | n | Code B | Empirical formula | MW | M.p.KB (°C.) | AgNO$_3$ titer of the hydrochloride |
|---|---|---|---|---|---|---|---|
| 32 | CH$_3$–CH(CH$_3$)–(CH$_2$)$_2$–O–C$_6$H$_4$– | 1 | 1414 | C$_{27}$H$_{41}$ClN$_2$O$_2$ | 461.09 | 142–144 | 100.2% |

The toxicopharmacological properties of the products forming the subject of the present invention are described below.

1. Acute Toxicity in Mice a) Principle

The products were administered orally to mice in a single dose. After a 14-day observation period, the mortality was recorded.

The results are expressed in the form of the 50% lethal dose (LD$_{50}$) in mg.kg$^{-1}$.

b) Results.

These are reported in Table I.

It can be seen that the products of the invention have a very low toxicity.

concentration must be doubled in order to obtain the same effect as in the absence of said product.

The logarithm of this concentration, with its sign changed, represents the pA$_2$ value of the product.

b) Results.

These are reported in Table II. They show that the products behave as competitive antagonists of norepinephrine at the alpha-adrenergic receptors, with an advantageous alpha-blocking activity.

3. Determination of the Alpha-Blocking Activity on Isolated Rabbit Ureter a) Principle Stimulation of the postsynaptic alpha-adrenergic receptors by norepinephrine causes contraction of the

TABLE I

| | | | | | | Acute toxicity in mice. | | | | | | | |
|---|---|---|---|---|---|---|---|---|---|---|---|---|---|
| PRODUCT | B.1055 | B.1057 | B.1079 | B.1105 | B.1115 | B.1152 | B.1168 | B 1178 | B.1184 | B.1191 | B.1204 | B.1206 | B.1213 | B.1256 |
| LD$_{50}$ mg·kg$^{-1}$ p.o | >1000 | >1000 | >1000 | ≈540 | >1000 | >1000 | >1000 | >1000 | >1000 | >1000 | >1000 | >1000 | >1000 | >1000 |
| PRODUCT | B.1261 | B 1299 | B.1326 | B.1338 | B.1340 | B.1343 | B.1353 | B.1356 | B.1358 | B 1362 | B.1387 | B.1393 | B.1399 |
| LD$_{50}$ mg·kg$^{-1}$ p.o | >1000 | >1000 | >1000 | >1000 | >1000 | >1000 | >1000 | >1000 | >1000 | 897 | >1000 | >1000 | ≈500 |

2. Determination of the Alpha-Blocking Activity on Isolated Rat Vas Deferens a) Principle.

Stimulation of the postsynaptic alpha-adrenergic receptors by norepinephrine causes contraction of the isolated vas deferens. The aim is to find the product concentration in whose presence the norepinephrine isolated rabbit ureter.

The aim is to find the product concentration in whose presence the contracting effect of a given norepinephrine concentration is halved by comparison with the contraction induced before the addition of said product.

The logarithm of this concentration, with its sign changed, represents the pD'$_2$ value.

b) Results

Some pD'$_2$ values are reported in Table II:

TABLE II

| | | | | | Alpha-blocking action of the products on isolated rat vas deferens. | | | | | | | |
|---|---|---|---|---|---|---|---|---|---|---|---|---|
| PRODUCT | B.1055 | B.1057 | B.1079 | B.1105 | B.1115 | B.1152 | B.1168 | B 1178 | B.1184 | B.1191 | B.1204 | B.1206 | B.1213 |
| pA$_2$ | 6.33 | 6.40 | <6 | 6.27 | 6.54 | N.D. insoluble | 6.71 | 7.14 | N.D. insoluble | 6.48 | 6.00 | 6.77 | 5.96 |
| PRODUCT | B.1256 | B.1261 | B 1299 | B.1326 | B.1338 | B.1340 | B.1343 | B.1353 | B.1356 | B.1358 | B 1362 | B.1387 | B.1393 | B.1399 |

TABLE II-continued

| Alpha-blocking action of the products on isolated rat vas deferens. | | | | | | | | | | | | | |
|---|---|---|---|---|---|---|---|---|---|---|---|---|---|
| $pA_2$ | <6 | 6.44 | 6.46 | <6 | 7.39 | <6 | 6.08 | <6 | <6 | <6 | <6 | 6.45 | <6 | 6.69* |

N.D. = Not Determined
*$pD'_2$

4. Determination of the Adrenolytic Activity "In Vivo" in Rats a) Principle

The intravenous injection of norepinephrine (0.4 mg.kg$^{-1}$) in wake rats causes the death of 100 percent of the animals. The prior administration of a substance with an alpha-blocking property makes it possible to reduce this toxicity.

The products claimed were administered orally 30 minutes before the intravenous injection of norepinephrine.

b) Results

These are expressed in the form of the 50% effective dose ($ED_{50}$), i.e. the dose, in mg.kg$^{-1}$, which protects 50 percent of the animals.

The $ED_{50}$ values corresponding to the products claimed are shown in Table III.

Compounds B.1168, B.1178, B.1299, B.1358, B.1387 and B.1399 provide excellent protection against the toxicity of norepinephrine, thus confirming the activity demonstrated on isolated organs.

ergic receptors and consequently had antihypertensive properties.

The molecules of the present invention also have properties of blocking the α-1 receptors, but they are particularly active on the lower urinary system and retain only a slight residual action on the heart.

The products according to the present invention therefore have very valuable pharmacological properties and their toxicity is sufficiently low to enable them to be used in therapy.

The products can therefore be employed in human or veterinary medicine, especially in the treatment of dysuria associated with ureteral hypertonia.

The products can be administered by a general route (parenteral, oral, rectal) or topically.

The pharmaceutical compositions in which at least one product according to the invention is present as the active ingredient, in combination with a pharmaceutically acceptable vehicle, can be solid or liquid and can take the form of, for example, injectable preparations, tablets, gelatin capsules or granules. The dosage can vary within wide limits, depending in particular on the

TABLE III

| Alpha-adrenolytic acitvity of the compounds "in vivo" in rats. | | | | | | | | | | | | | |
|---|---|---|---|---|---|---|---|---|---|---|---|---|---|
| PRODUCT | B.1055 | B.1057 | B.1079 | B.1105 | B.1115 | B.1152 | B.1168 | B 1178 | B.1184 | B.1191 | B.1204 | B.1206 | B.1213 | B.1256 |
| $ED_{50}$ mg · kg$^{-1}$ | >100 | >100 | >100 | 200 | 200 | >100 | 3 | 2 | >100 | >100 | 56 | 100 | 15 | 121 |
| PRODUCT | B.1261 | B 1299 | B.1326 | B.1338 | B.1340 | B.1343 | B.1353 | B.1356 | B.1358 | B 1362 | B.1387 | B.1393 | B.1399 |
| mg · kg$^{-1}$ | 20 | 10 | >200 | 6.4 | 11.3 | 142 | 30.9 | 31.1 | 2.1 | 37.3 | 6.78 | >200 | 0.78 |

5. Activity on Ureteral Hyperpressure in Rabbits a) Principle

An increase in the arterial pressure and the ureteral pressure is induced in anesthetized rabbits by an intravenous injection of norepinephrine. These hyperpressures can be inhibited by the prior administration of molecules with alpha-blocking potential.

The efficacy is assessed by the 50% inhibitory dose ($ID_{50}$), i.e. the dose which inhibits the increases in arterial and ureteral pressures by 50 percent. Comparison of the $ID_{50}$ values for both cases makes it possible to demonstrate a possible ureteral specificity.

b) Results

These are shown in Table IV below.

TABLE IV

| Product | $ID_{50}$ mg · kg$^{-1}$ I.V. | | $R = \frac{\text{Arterial}}{\text{Ureteral}}$ |
|---|---|---|---|
| | Arterial pressure | Ureteral pressure | |
| B 1178 | 3.9 | 0.37 | 10.6 |
| B 1338 | 18.98 | 1.6 | 11.8 |
| B 1358 | 5 | 1.22 | 4.1 |
| B 1399 | 1.64 | 0.18 | 9.1 |

These results show the greater efficacy of these compounds on the ureteral pressure than on the arterial pressure.

Similar molecules have already been described. They had properties of blocking the cardiac α-1 and β-adrentype and severity of the complaint to be treated and on the mode of administration.

Most frequently, the adult dosage is between 0.1 and 0.5 g per day by parenteral administration and between 0.25 and 4 g per day by oral administration.

Such pharmaceutical compositions form a subject of the invention. Their method of preparation forms a further subject of the invention.

Said method consists in mixing an effective dose of a compound of formula (I) with suitable excipients.

The invention finally relates to the use of the compounds of formula (I) for the preparation of drugs which are useful for the treatment of dysuria associated with ureteral hypertonia.

What is claimed is:

1. A product of the formula:

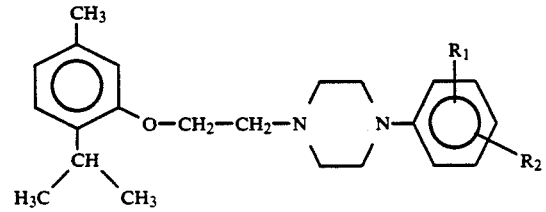

in which $R_1$ is selected from a hydrogen atom, a halogen atom, a hydroxyl radical, an alkyl radical having from 1 to 4 carbon atoms, an alkoxy radical having from 1 to 5 carbon atoms or a phenoxy, benzyloxy, trifluoromethyl or acetyl radical and $R_2$ is selected from a hydrogen atom, a halogen atom, a hydroxyl radical, an alkyl radical having from 1 to 4 carbon atoms, an alkoxy radical having from 1 to 5 carbon atoms or a phenoxy, benzyloxy, trifluoromethyl or acetyl radical.

2. A drug useful in therapy of the urinary system containing a therapeutically effective amount of at least one compound according to claim 1.

3. A drug useful in the treatment of dysuria associated with ureteral hypertonia, containing a therapeutically effective amount of at least one compound according to claim 1.

UNITED STATES PATENT AND TRADEMARK OFFICE
CERTIFICATE OF CORRECTION

PATENT NO.   : 5,110,816
DATED        : May 5, 1992
INVENTOR(S)  : Patrick Houziaux, Jean-Pierre Riffaud, Jean-Yves Lacolle and Bernard Danree It is certified that error appears in the above-identified patent and that said Letters Patent is hereby corrected as shown below:

Column 2 Line 63 "ethoxyl]" should read --ethoxy]--.

Column 6 Line 25 ",IR" should read --, IR--.

Column 6 Line 31 "phenylpiperazine" should read --phenylpiperazin--.

Column 7 Line 57 "ethoxyl]" should read --ethoxy]--.

Column 8 Line 41 "ethoxyl]" should read --ethoxy]--.

Column 11 Line 44 "X" should read --=--.

Column 15 Ex. 12 Column R, drawing should have dots at corners.

Signed and Sealed this

Seventeenth Day of August, 1993

Attest:

BRUCE LEHMAN

Attesting Officer

Commissioner of Patents and Trademarks